United States Patent
Kuznetsov et al.

(10) Patent No.: US 9,441,944 B2
(45) Date of Patent: Sep. 13, 2016

(54) REGENERATIVE MODE LOCKED LASER SWEPT SOURCE FOR OCT MEDICAL IMAGING

(75) Inventors: Mark E. Kuznetsov, Lexington, MA (US); Bartley C. Johnson, North Andover, MA (US)

(73) Assignee: Axsun Technologies LLC, Billerica, MA (US)

( * ) Notice: Subject to any disclaimer, the term of this patent is extended or adjusted under 35 U.S.C. 154(b) by 509 days.

(21) Appl. No.: 13/473,243

(22) Filed: May 16, 2012

(65) Prior Publication Data

US 2013/0308136 A1     Nov. 21, 2013

(51) Int. Cl.
| | |
|---|---|
| *G01B 9/02* | (2006.01) |
| *H01S 5/065* | (2006.01) |
| *H01S 5/0683* | (2006.01) |
| *H01S 5/14* | (2006.01) |
| *G01N 21/47* | (2006.01) |
| *H01S 5/022* | (2006.01) |
| *H01S 5/024* | (2006.01) |
| *A61B 5/00* | (2006.01) |

(52) U.S. Cl.
CPC ....... *G01B 9/02004* (2013.01); *G01B 9/02091* (2013.01); *G01N 21/4795* (2013.01); *H01S 5/0657* (2013.01); *H01S 5/0683* (2013.01); *H01S 5/142* (2013.01); *A61B 5/0066* (2013.01); *H01S 5/02216* (2013.01); *H01S 5/02248* (2013.01); *H01S 5/02284* (2013.01); *H01S 5/02415* (2013.01)

(58) Field of Classification Search
USPC ................ 356/479, 497; 372/18, 20, 29.011
See application file for complete search history.

(56) References Cited

U.S. PATENT DOCUMENTS

| | | | | |
|---|---|---|---|---|
| 3,339,073 | A | * | 8/1967 | Hunter ......................... 359/238 |
| 3,586,997 | A | * | 6/1971 | Kinsel .............................. 372/18 |
| 3,815,046 | A | * | 6/1974 | Johnson et al. ................ 372/12 |
| 4,081,765 | A | * | 3/1978 | Berg et al. ....................... 372/24 |
| 4,918,396 | A | | 4/1990 | Halemane et al. |
| 5,509,022 | A | | 4/1996 | Lowery et al. |
| H0001813 | H | * | 11/1999 | Kersey ............................ 372/94 |

(Continued)

FOREIGN PATENT DOCUMENTS

| | | |
|---|---|---|
| JP | 2002-511199 A | 4/2002 |
| JP | 2002-164614 A | 6/2002 |

(Continued)

OTHER PUBLICATIONS

Abedin, K. S. et al., "Beat-Spectrum Tailoring of Fiber Lasers Using an Intracavity Fabry-Perot Filter for Regenerative and Harmonic Mode-Locking," IEEE Photonics Technology Letters, vol. 11, No. 7, Jul. 1999, pp. 800-802.

(Continued)

*Primary Examiner* — Tarifur Chowdhury
*Assistant Examiner* — Jonathon Cook
(74) *Attorney, Agent, or Firm* — HoustonHogle LLP

(57) ABSTRACT

An optical coherence analysis system uses a laser swept source that is constrained to operate in a mode locked condition using regenerative mode-locking. This is accomplished by synchronously changing the laser cavity's net gain and/or phase based on time varying intensity of the swept optical signal generated by the laser. This produces a stable pulsation behavior, which is associated with smooth tuning (low optical frequency reference clock jitter) and low relative intensity noise (RIN).

15 Claims, 14 Drawing Sheets

(56) References Cited

U.S. PATENT DOCUMENTS

| | | | |
|---|---|---|---|
| 6,044,097 A | 3/2000 | Kawamura et al. | |
| 6,192,058 B1 | 2/2001 | Abeles | |
| 6,345,059 B1 | 2/2002 | Flanders | |
| 6,366,592 B1* | 4/2002 | Flanders | 372/18 |
| 6,373,632 B1 | 4/2002 | Flanders | |
| 6,501,551 B1* | 12/2002 | Tearney | A61B 1/00096 356/477 |
| 6,608,711 B2 | 8/2003 | Flanders et al. | |
| 6,816,515 B1 | 11/2004 | Yun et al. | |
| 7,139,078 B2 | 11/2006 | Hogan | |
| 7,414,779 B2* | 8/2008 | Huber et al. | 359/333 |
| 7,415,049 B2 | 8/2008 | Flanders et al. | |
| 7,701,982 B2 | 4/2010 | Yu et al. | |
| 7,733,923 B2 | 6/2010 | Doerr | |
| 7,813,388 B2 | 10/2010 | Park et al. | |
| 8,059,277 B2 | 11/2011 | Atia et al. | |
| 8,285,368 B2 | 10/2012 | Chen et al. | |
| 8,384,909 B2 | 2/2013 | Yun et al. | |
| 8,494,016 B2 | 7/2013 | Karni et al. | |
| 2002/0064353 A1 | 5/2002 | Yokoyama | |
| 2003/0179790 A1* | 9/2003 | Bouda et al. | 372/20 |
| 2004/0100675 A1 | 5/2004 | Matsko et al. | |
| 2005/0018714 A1 | 1/2005 | Fermann et al. | |
| 2006/0109873 A1* | 5/2006 | Crosson et al. | 372/19 |
| 2006/0187537 A1* | 8/2006 | Huber et al. | 359/337.22 |
| 2007/0268939 A1* | 11/2007 | Cattellan et al. | 372/20 |
| 2007/0297462 A1 | 12/2007 | Jalali et al. | |
| 2009/0059970 A1 | 3/2009 | Atia et al. | |
| 2009/0067456 A1 | 3/2009 | Villeneuve et al. | |
| 2009/0107962 A1* | 4/2009 | Munroe et al. | 219/121.67 |
| 2009/0174931 A1 | 7/2009 | Huber et al. | |
| 2009/0290167 A1 | 11/2009 | Flanders et al. | |
| 2010/0210952 A1 | 8/2010 | Taira et al. | |
| 2011/0155916 A1 | 6/2011 | Furusawa et al. | |
| 2011/0216325 A1* | 9/2011 | Schmitt | 356/479 |
| 2012/0162662 A1 | 6/2012 | Johnson et al. | |
| 2012/0219026 A1* | 8/2012 | Saracco et al. | 372/21 |

FOREIGN PATENT DOCUMENTS

| | | |
|---|---|---|
| JP | 2007-229310 A | 9/2007 |
| JP | 2009-049123 A | 3/2009 |
| JP | WO2009133734 A1 | 5/2009 |
| JP | 2009-277754 A | 11/2009 |
| JP | 2010-010172 A | 1/2010 |
| JP | 2011-524003 A | 8/2011 |
| WO | 9956360 A1 | 11/1999 |
| WO | 2009/139481 A1 | 11/2009 |
| WO | 2010/111795 A1 | 10/2010 |

OTHER PUBLICATIONS

Bilenca, A. et al., "Numerical study of wavelength-swept semiconductor ring lasers: the role of refractive-index nonlinearities in semiconductor optical amplifiers and implications for biomedical imaging applications," Optics Letters, vol. 31, No. 6, Optical Society of America, Mar. 15, 2006, pp. 760-762.

Choma, M. et al., "Sensitivity advantage of swept source and Fourier domain optical coherence tomography," Optics Express, vol. 11, No. 18, Optical Society of America, Sep. 8, 2003, pp. 2183-2189.

Chong, C. et al., "Large coherence length swept source for axial length measurement of the eye," Applied Optics, vol. 48, No. 10, Optical Society of America, Apr. 1, 2009, pp. D144-D150.

Chong, C. et al., "Spectral narrowing effect by quasi-phase continuous tuning in high-speed wavelength-swept light source," Optics Express, vol. 16, No. 25, Optical Society of America, Dec. 8, 2008, pp. 21105-21118.

De Boer, J. et al., "Improved signal-to-noise ratio in spectral-domain compared with time-domain optical coherence tomography," Optics Letters, vol. 28, No. 21, Optical Society of America, Nov. 1, 2003, pp. 2067-2069.

Braaf, B. et al., "Phase-stabilized optical frequency domain imaging at 1-μm for the measurement of blood flow in the human choroid," Optics Express, vol. 19, No. 22, Oct. 24, 2011, pp. 20886-20903.

Dhalla, Al-H. et al., "Complete complex conjugate resolved heterodyne swept-source optical coherence tomography using a dispersive optical delay line," Biomedical Optics Express, vol. 2, No. 5, Optical Society of America, Apr. 15, 2011, pp. 1218-1232.

Dhalla, Al-H. et al., "Complex conjugate resolved heterodyne swept source optical coherence tomography using coherence revival," Biomedical Optics Express, vol. 3, No. 3, Mar. 1, 2012, pp. 633-649.

Eigenwillig, C. et al., "K-space linear Fourier domain mode locked laser and applications for optical coherence tomography," Optics Express, vol. 16, No. 12, Optical Society of America, Jun. 9, 2008, pp. 8916-8937.

Goldberg, B. et al., "Miniature swept source for point of care Optical Frequency Domain Imaging," Optics Express, vol. 17, No. 5, Optical Society of America, Mar. 2, 2009, pp. 3619-3629.

Haus, H. A., "Mode-Locking of Lasers," IEEE Journal on Selected Topics in Quantum Electronics, vol. 6, No. 6, Nov./Dec. 2000, pp. 1173-1185.

Hee, M. et al., "Femtosecond transillumination optical coherence tomography," Optics Letters, vol. 18, No. 12, Jun. 15, 1993, pp. 950-952.

Huber, R. et al., "Amplified, frequency swept lasers for frequency domain reflectometry and OCT imaging: design and scaling principles," Optics Express, vol. 13, No. 9, Optical Society of America, May 2, 2005, pp. 3513-3528.

Huber, R. et al., "Fourier Domain Mode Locking (FDML): A new laser operating regime and applications for optical coherence tomography," Optics Express, vol. 14, No. 8, Optical Society of America, Apr. 17, 2006, pp. 3225-3237.

Huang, S. et al., "Swept source optical coherence microscopy using a Fourier domain mode-locked laser," Optics Express, vol. 15, No. 10, Optical Society of America, May 14, 2007, pp. 6210-6217.

Huo, L. et al., "Self-regenerative FDML for OCT imaging," presented at SPIE Photonics West—BiOS conference, Session 8. No. 7889-50., Jan. 25, 2011.

Jenkins, M. et al., "Ultrahigh-speed optical coherence tomography imaging and visualization of the embryonic avian heart using a buffered Fourier Domain Mode Locked laser," Optics Express, vol. 15, No. 10, Optical Society of America, May 14, 2007, pp. 6251-6267.

Kafka, J. D. et al., "Picosecond and Femtosecond Pulse Generation in a Regeneratively Mode-Locked Ti : Sapphire Laser," IEEE Journal of Quantum Electronics, vol. 28, No. 10, Oct. 1992, pp. 2151-2162.

Kuznetsov, M. et al., "Compact Ultrafast Reflective Fabry-Perot Tunable Lasers for OCT Imaging Applications," SPIE BIOS, RFPTL Lasers for OCT, Jan. 26, 2010, 21 pages.

Kuznetsov, M. et al., "Compact Ultrafast Reflective Fabry-Perot Tunable Lasers for OCT Imaging Applications," SPIE, vol. 7554, 2010, pp. 75541F-1-75541F-6.

Leitgeb, R. et al., "Performance of fourier domain vs. time domain optical coherence tomography," Optics Express, vol. 11, No. 8, Optical Society of America, Apr. 21, 2003, pp. 889-894.

Margalit, M. et al., "Harmonic Mode-Locking Using Regenerative Phase Modulation," IEEE Photonics Technology Letters, vol. 10, No. 3, Mar. 1998, pp. 337-339.

Murari, K. et al., "Self-starting, self-regulating Fourier domain mode locked fiber laser for OCT imaging," Biomedical Optics Express, vol. 2, No. 7, Optical Society of America, Jun 22, 2011, pp. 2005-2011.

Nakazawa, M. et al., "Ultrastable harmonically and regeneratively modelocked polarisation-maintaining erbium fibre ring laser," Electronic Letters, vol. 30, No. 19, Sep. 15, 1994, pp. 1603-1605.

Sutter, D. et al., "Semiconductor saturable-absorber mirror-assisted Kerr-lens mode-locked Ti:sapphire laser producing pulses in the two-cycle regime," Optics Letters, vol. 24, No. 9, Optical Society of America, May 1, 1999, pp. 631-633.

Tsuchida, H., "160-Gb/s Optical Clock Recovery Using a Regeneratively Mode-Locked Laser Diode," IEEE Photonics Technology Letters, vol. 18, No. 16, Aug. 15, 2006, pp. 1687-168.

(56) References Cited

OTHER PUBLICATIONS

Yan, C. et al., "Picosecond Semiconductor Lasers Based on Regenerative Feedback Schemes," Center for High Technology Materials, The University of New Mexico, Albuquerque, NM 87131, pp. 286-289.

Yun, S. et al., "Extended-Cavity Semiconductor Wavelength-Swept Laser for Biomedical Imaging," IEEE Photonics Technology Letters, vol. 16, No. 1, Jan. 2004, pp. 293-295.

Yun, S. et al., "High-speed optical frequency-domain imaging," Optics Express, vol. 11, No. 22, Optical Society of America, Nov. 3, 2003, pp. 2953-2963.

Yun, S. et al., "High-speed wavelength-swept semiconductor laser with a polygon-scanner-based wavelength filter," Optics Letters, vol. 28, No. 20, Optical Society of America, Oct. 15, 2003, pp. 1981-1983.

Yun, S. et al., "Wavelength Swept Lasers," Optical Coherence Tomography, Springer-Verlag Berlin Heidelberg, 2008, pp. 359-377.

Yun, S. et al., "Removing the depth-degeneracy in optical frequency domain imaging with frequency shifting," Optics Express, vol. 12, No. 20., Optical Society America, Oct. 4, 2004, pp. 4822-4828.

Avrutin, Eugene A., et al., "Travelling wave modeling and dynamic properties of short external cavity semiconductor lasers with fast intracavity frequency sweeping for biomedical imaging applications," Dept. of Electronics, University of York, York Y0105DD, UK, Submitted to the IEEE Journal of Selected Topics in Quantum Electronics, JSTQE 2013, pp. 1-8.

International Search Report, mailed Apr. 3, 2012, from International Application No. PCT/US2011/067413 filed on Dec. 27, 2011.

Eckstein et al., "High-Resolution Two-Photon Spectroscopy with Picosecond Light Pulses", Phys. Rev. Lett., vol. 40, 1978, pp. 847-850.

International Preliminary Report on Patentability, mailed on Jul. 11, 2013, for related International Application No. PCT/US2011/067413, filed on Dec. 27, 2011.

Wang, F. et al., "Wideband-tuneable, nanotube mode-locked, fibre laser," Nature Nanotechnology, vol. 3, Macmillan Publishers Limited, Dec. 2008, pp. 738-742.

* cited by examiner

REGENERATIVE MODE LOCKED LASER SWEPT SOURCE FOR OCT MEDICAL IMAGING

BACKGROUND OF THE INVENTION

Optical coherence analysis relies on the use of the interference phenomena between a reference wave and an experimental wave or between two parts of an experimental wave to measure distances and thicknesses, and calculate indices of refraction of a sample. Optical Coherence Tomography (OCT) is one example technology that is used to perform high-resolution cross sectional imaging. It is often applied to imaging biological tissue structures, for example, on microscopic scales in real time. Optical waves are reflected from an object or sample and a computer produces images of cross sections of the object by using information on how the waves are changed upon reflection.

Fourier domain OCT (FD-OCT) currently offers the best performance for many applications. Moreover, of the Fourier domain approaches, swept-source OCT has distinct advantages over techniques such as spectrum-encoded OCT because it has the capability of balanced and polarization diversity detection. It has advantages as well for imaging in wavelength regions where inexpensive and fast detector arrays, which are typically required for spectrum-encoded FD-OCT, are not available.

In swept source OCT, the spectral components are not encoded by spatial separation, but they are encoded in time. The spectrum is either filtered or generated in successive frequency steps and reconstructed before Fourier-transformation. Using the frequency scanning swept source, the optical configuration becomes less complex but the critical performance characteristics now reside in the source and especially its frequency tuning speed and accuracy.

High speed frequency tuning for OCT swept sources is especially relevant to in vivo imaging where fast imaging reduces motion-induced artifacts and reduces the length of the patient procedure. It can also be used to improve resolution.

The swept sources for OCT systems have typically been tunable lasers. The advantages of tunable lasers include high spectral brightness and relatively simple optical designs. A tunable laser is constructed from a gain medium, such as a semiconductor optical amplifier (SOA) that is located within a resonant cavity, and a tunable element such as a rotating grating, grating with a rotating mirror, or a Fabry-Perot tunable filter. Currently, some of the highest tuning speed lasers are based on the laser designs described in U.S. Pat. No. 7,415,049 B1, entitled Laser with Tilted Multi Spatial Mode Resonator Tuning Element, by D. Flanders, M. Kuznetsov and W. Atia. The use of micro-electro-mechanical system (MEMS) Fabry-Perot tunable filters combines the capability for wide spectral scan bands with the low mass, high mechanical resonant frequency deflectable MEMS membranes that have the capacity for high speed tuning.

Certain tradeoffs in laser design, however, can be problematic for OCT systems. Generally, shorter laser cavities translate to higher potential tuning speeds, since laser oscillation must build up anew from spontaneous emission when the laser is tuned. Thus, round-trip travel time for the light in the laser cavities should be kept low so that this build up occurs quickly. Short laser cavities, however, create problems in terms of the spectral spacing of the longitudinal cavity modes of the laser. That is, lasers can only produce light at frequencies which are integer multiples of the cavity mode spacing since the light must oscillate within the cavities. Shorter cavities result in fewer and more widely spaced modes. This results in greater mode hopping noise as the laser is tuned over these discrete cavity modes. So, when designing an OCT laser, there is typically a need to choose between low noise and high speed.

One laser design seeks to address this drawback. A Fourier-domain mode-locked laser (FDML) stores light in a long length of fiber for amplification and recirculation in synchronism with the laser's tuning element. See "Fourier Domain Mode Locking (FDML): A new laser operating regime and applications for optical coherence tomography", R. Huber, M. Wojtkowski, and J. G. Fujimoto, 17 Apr. 2006/Vol. 14, No. 8/OPTICS EXPRESS 3225. The drawback of these devices is their complexity, however. Moreover, the ring cavity including the long storage fiber creates its own performance problems such as dispersion and stability.

SUMMARY OF THE INVENTION

Research with swept tunable lasers has shown that when they are operated at high sweep rates they tend to operate in a mode locked regime. In a mode locked regime optical power of the laser varies on a time scale of the cavity roundtrip time as one or more optical pulses travel in the laser cavity, as is found in a traditional mode locked laser. The pulse repetition rate is close to the laser cavity roundtrip time or to a typically small, say a factor of 2 to 10, multiple. Since this mode locking arises from frequency tuning of the laser, it is termed swept mode locking.

This mode locked regime can have the effect of actually facilitating the high-speed tuning of the laser. A four-wave mixing effect red shifts the wave in the laser cavity. This facilitates the tuning to lower optical frequencies. See A. Bilenca, S. H. Yun, G. J. Tearney, and B. E. Bouma, "Numerical study of wavelength-swept semiconductor ring lasers: the role of refractive-index nonlinearities in semiconductor optical amplifiers and implications for biomedical imaging applications", OPTICS LETTERS/Vol. 31, No. 6/Mar. 15, 2006.

Problems, however, often arise when tuning to higher optical frequencies and also during very high speed tuning. Generally, this tuning tends to be more unstable. Some of these instabilities probably result from the fact that the laser cavity is changing through the process of tuning, and thus the characteristics that instigate the swept mode locking also change. As a result, the lasers can flip to other swept mode locked regimes during a single frequency scan of the tunable laser. For example, during the sweep, the number of pulses circulating in the cavity can change, causing the lasers to behave chaotically and unpredictably as they move between the different regimes. The different regimes can result in different performance characteristics as the tunable lasers relate to the OCT systems in which they operate.

The present invention concerns a swept tunable laser source. During its swept operation, it is constrained to operate in a controlled mode locked regime by using the time-varying intensity of the swept optical signal as feedback to control the mode-locked operation of laser swept source. In the illustrated embodiments, this is accomplished by actively modulating cavity gain and/or intracavity elements. This has the effect of stabilizing the emission characteristics of the laser and avoids noisy disruptions due to uncertainty or flips in the number of pulses circulating in the cavity. Instead, the mode locking system stabilizes the pulsation behavior of the laser by modulating a gain, for example, of the cavity of the laser at a harmonic of the cavity round trip frequency that is instantaneously measured by time-varying intensity of the swept optical signal as feedback to control the mode-locked operation of laser swept source.

In other embodiments described below, the stabilization is accomplished by modulating an intracavity phase modulator or a lossy element within the cavity. In still other embodiments, stabilization is facilitated with an intracavity saturable absorber, for example. As a result, in some cases operation in a stable mode locked regime can facilitate not only the tuning to lower optical frequencies, but also high speed tuning to higher optical frequencies to thereby enable stable and smooth up and down tuning.

Other useful mode-locking methods include active gain modulation through current injection or synchronous pumping, active loss modulation, active phase modulation and passive mode locking. Active phase modulation allows for both short-to-long and long-to-short tuning directions.

Gated mode locking can be used to select one pulse per round trip in cases where the laser naturally tends to emit more than one.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same or similar parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
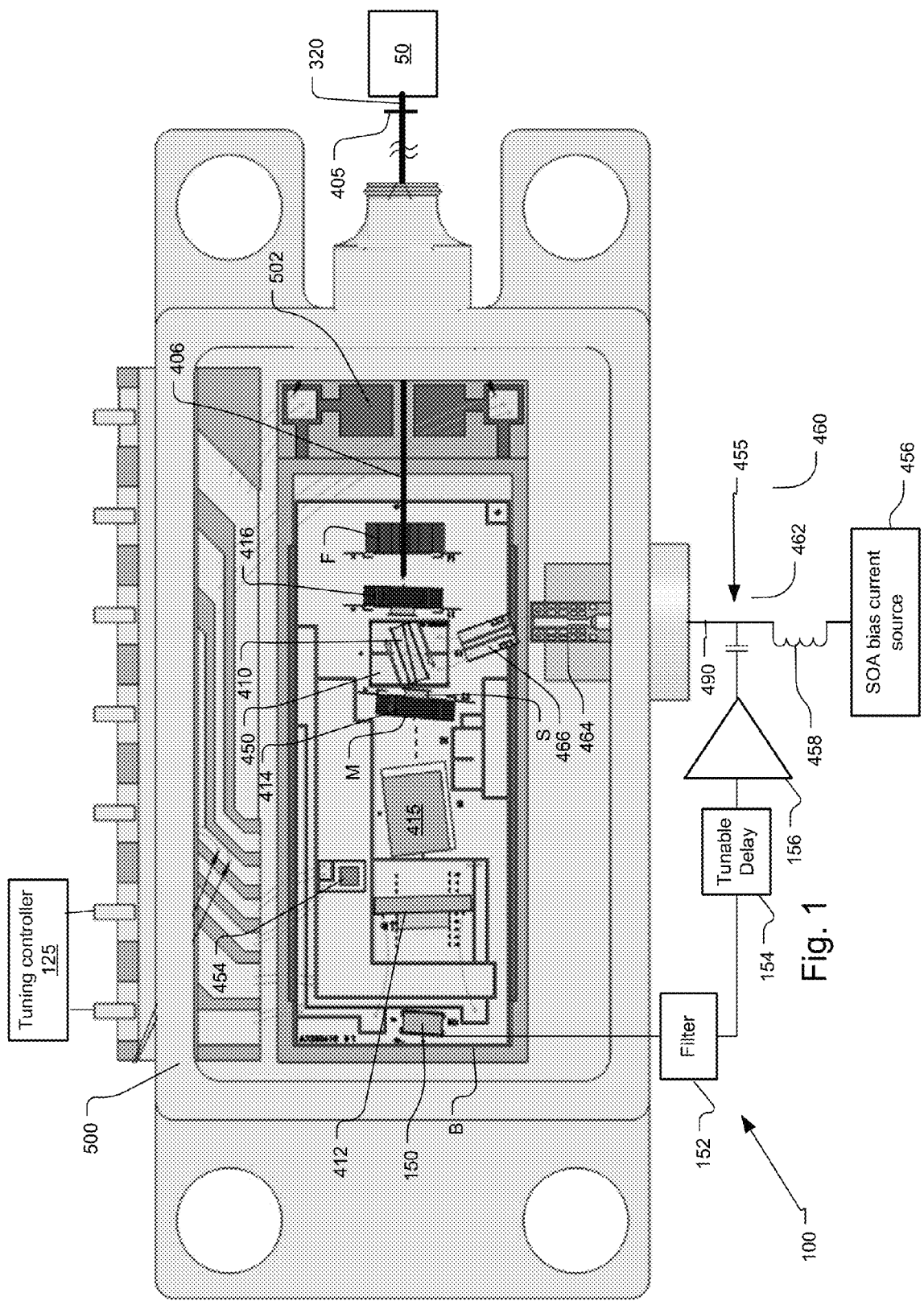
FIG. 1 is a top plan scale drawing of regenerative mode-locked laser swept source for optical coherence analysis according to a first embodiment the present invention.

FIG. 1 shows regenerative mode-locked laser swept source 100 for optical coherence analysis, which has been constructed according to the principles of the present invention. This embodiment controls or stabilizes the mode-locked operation by modulating the bias current to an intracavity gain element in response to the time-varying intensity of the swept optical signal that is generated by the laser swept source 100.

In the current embodiment, the laser swept source 100 is preferably a laser as generally described in incorporated U.S. Pat. No. 7,415,049 B1. It includes a linear cavity with a gain element 410 and a frequency tuning element 412, which are preferably implemented on a common optical bench B. In the illustrated example, the frequency tuning element is a reflective Fabry-Perot filter, which defines one end of the cavity, in the illustrated implementation and thus also functions as an end reflector of the laser cavity.

In other embodiments, other cavity configurations are used such as ring cavities. Further other cavity frequency tuning elements are used such as gratings and thin-film filters. In some examples, these tuning elements are mechanically tuned such as rotated or pivoted. These elements can also be located entirely within the cavity such as an angle isolated transmissive Fabry-Perot tunable filter or grating.

Currently, the passband of the Fabry-Perot filter 412 is between 1 and 10 GHz and is tuned over a tuning band or scan band of greater than 10 nanometers (nm), and is usually greater than 50 or 100 nm.

In more detail with respect to the current embodiment, the tunable laser 100 comprises a semiconductor gain chip 410 that is paired with a micro-electro-mechanical (MEMS) angled reflective Fabry-Perot tunable filter 412, which defines one end of the laser cavity. The cavity extends to a second output reflector 405 that is located at the end of a fiber pigtail 406 that is coupled to the bench B and also forms part of the cavity.

Currently, the length of the cavity is at least 40 millimeters (mm) long and preferably over 50 to 80 mm. This ensures close longitudinal mode spacing that reduces mode hopping noise.

In other embodiments, shorter cavities are used. In some of these embodiments, very short cavities with wider passband tuning elements (filters) 412 are used for extremely high speed applications where only short coherence lengths are required. In some of these examples, the passband of the Fabry-Perot filter 412 is between 20 and 40 GHz, or wider. The length of the laser cavity is less than 20 mm or 10 mm, and thus may not extend into optical fiber, but is entirely implemented on the bench B.

Nevertheless, the length of the cavity in any of these embodiments is relatively short when compared with FDML lasers. The cavity lengths in FDML lasers tend to be in the kilometer range. In contrast, almost all of the embodiments of the present laser have cavities of less than a meter long.

The tunable or swept optical signal passing through the output reflector 405 is transmitted on optical fiber 320 or via free space to an interferometer 50 of the OCT system.

The semiconductor optical amplifier (SOA) chip gain element 410 is located within the laser cavity. In the current embodiment, input and output facets of the SOA chip 410 are angled and anti-reflection (AR) coated, providing typically parallel beams from the two facets. In the preferred embodiment, the SOA chip 410 is bonded or attached to the common bench B via a submount 450.

The material system of the chip 410 is selected based on the desired spectral operating range. Common material systems are based on III-V semiconductor materials, including binary materials, such as GaN, GaAs, InP, GaSb, InAs, as well as ternary, quaternary, and pentenary alloys, such as InGaN, InAlGaN, InGaP, AlGaAs, InGaAs, GaInNAs, GaInNAsSb, AlInGaAs, InGaAsP, AlGaAsSb, AlGaInAsSb, AlAsSb, InGaSb, InAsSb, and InGaAsSb. Collectively, these material systems support operating wavelengths from about 400 nanometers (nm) to 2000 nm, including longer wavelength ranges extending into multiple micrometer wavelengths. Semiconductor quantum well and quantum dot gain regions are typically used to obtain especially wide gain and spectral emission bandwidths. Currently, edge-emitting chips are used although vertical cavity surface emitting laser (VCSEL) chips are used in different implementations.

The use of a semiconductor chip gain medium 410 has advantages in terms of system integration since semiconductor chips can be bonded to submounts that in turn are directly bonded to the bench B. Other possible gain media can be used in other implementations, however. Such examples include solid state gain media, such as rare-earth (e.g., Yb, Er, Tm) doped bulk glass, waveguides or optical fiber. Generally, however, these media have longer lifetimes, which make them less suitable according to the current theory.

Each facet of the SOA 410 has an associated lens structure 414, 416 that is used to couple the light exiting from either facet of the SOA 410 in the illustrated free-space version of the laser. The first lens structure 414 couples the light between the back facet of the SOA 410 and the reflective Fabry-Perot tunable filter 412. Light exiting out the output or front facet of the SOA 410 is coupled by the second lens structure 416 to a fiber end facet of the pigtail 406.

In a current implementation, each lens structure comprises a LIGA mounting structure M, which is deformable to enable post installation alignment, and a transmissive substrate S on which the lens is formed. The transmissive substrate S is typically solder or thermocompression bonded to the mounting structure M, which in turn is solder bonded to the optical bench B.

The fiber facet of the pigtail 406 is also preferably mounted to the bench B via a fiber mounting structure F, to which the fiber 406 is solder bonded. The fiber mounting structure F is likewise usually solder bonded to the bench B. Deformable fiber mounting structure F typically allows post installation alignment of the fiber for optimal coupling of light from the SOA chip to the fiber.

The angled reflective Fabry-Perot filter 412 is a multi-spatial-mode tunable filter that provides angular dependent reflective spectral response back into the laser cavity. This characteristic is discussed in more detail in incorporated U.S. Pat. No. 7,415,049 B1.

Preferably, the tunable filter 412 is a Fabry-Perot tunable filter that is fabricated using micro-electro-mechanical systems (MEMS) technology and is attached, such as directly solder bonded, to the bench B. Currently, the filter 412 is manufactured using technologies described in U.S. Pat. Nos. 6,608,711 or 6,373,632, which are incorporated herein by this reference. A curved-flat resonator structure is used in which a generally flat mirror and an opposed curved mirror define a filter optical cavity, the optical length of which is modulated by electrostatic deflection of at least one of the mirrors.

The regenerative mode-locked laser swept source 100 and the other embodiments discussed hereinbelow are generally intended for high speed tuning to generate tunable swept optical signals that scan over the tuning band or scanband at speeds greater than 1 kiloHertz (kHz). In current embodiments, the regenerative mode-locked laser swept source 100 tunes over the scanband at speeds greater than 50 or 100 kHz. In very high speed embodiments, the mode-locked laser swept source 100 tunes at speeds greater than 200 or 500 kHz.

The tuning controller 125 provides a tuning voltage function to the Fabry-Perot filter 412, which includes a membrane that is electrostatically deflectable to thereby sweep the filter optical passband across the tuning band, preferably with optical frequency varying linearly with time. Typically, the width of the tuning band is greater than 10 nm. In the current embodiments, it is preferably between 50 and 150 nm, although even wider tuning bands are contemplated in some examples.

The tuning speed provided by the tuning controller 125 is also expressed in wavelength per unit time. In one example, for an approximately 110 nm tuning band or scanband and 100 kHz scan rate, assuming 60% duty cycle for substantially linear up-tuning, the peak sweep speed would be 110 nm*100 kHz/0.60=18,300 nm/msec=18.3 nm/µsec or faster. In another example, for an approximately 90 nm tuning range and 50 kHz scan rate, assuming a 50% duty cycle for substantially linear up-tuning, the peak sweep speed is 90 nm*50 kHz/0.50=9,000 nm/msec=9.0 nm/µsec or faster. In a smaller tuning band example having an approximately 30 nm tuning range and 2 kHz scan rate, assuming a 80% duty cycle for substantially linear tuning, the peak sweep speed would be 30 nm*2 kHz/0.80=75 nm/msec=0.075 nm/µsec, or faster.

Thus, in terms of scan rates, in the preferred embodiments described herein, the sweep speeds are greater than 0.05 nm/µsec, and preferably greater than 5 nm/µsec. In still higher speed applications, the scan rates are higher than 10 nm/µsec.

In one implementation, an extender element 415 is added to the laser cavity. This is fabricated from a transparent, preferably high refractive index material, such as fused silica, silicon, GaP or other transmissive material having a refractive index of ideally about 1.5 or higher. Currently silicon or GaP is preferred. Both endfaces of the extender element 415 are antireflection coated. Further, the element 415 is preferably angled by between 1 and 10 degrees relative to the optical axis of the cavity to further spoil any reflections from the endfaces from entering into the laser beam optical axis.

The extender element 415 is used to change the optical distance between the laser intracavity spurious reflectors and thus change the depth position of the spurious peaks in the image while not necessitating a change in the physical distance between the elements.

The bench B is termed a micro-optical bench and is preferably less than 10 millimeters (mm) in width and about 25 mm in length or less. This size enables the bench to be installed in a standard, or near standard-sized, butterfly or DIP (dual inline pin) hermetic package 500. In one implementation, the bench B is fabricated from aluminum nitride. A thermoelectric cooler 502 is disposed between the bench B and the package 500 (attached/solder bonded both to the backside of the bench and inner bottom panel of the package) to control the temperature of the bench B. The bench temperature is detected via a thermistor 454 installed on the bench B.

The regenerative mode locking system of the illustrated embodiment includes a detector 150 to enable the detection of the time-varying intensity of the swept optical signal that is generated in the laser cavity.

In the illustrated embodiment, the detector 150 is located to detect light transmitted through the tunable filter 412. In other examples, the detector 150 detects the time-varying intensity of the swept optical signal using an intracavity tap located within the laser cavity. In still other examples, the time-varying intensity of the swept optical signal is detected via a fiber coupler on pigtail 406 or optical fiber 320.

In any event, the detector 150 is preferably located in close physical proximity to the laser cavity or at least the optical distances and thus the optical delay is known and stable over time and temperature. This is required since the electrical response of the detector 150 is used to control the mode-locked behavior of the tunable laser 100. The close physical proximity ensures that the electrical response of the detector 150 can be used to synchronously modulate elements in the laser cavity to stabilize and control the pulses that are generated within the cavity due to the swept mode-locking behavior during the scanning of the swept optical signal over the tuning band.

In other examples, the transmitted light is further provided to a k-clock subsystem as disclosed in U.S. Pat. Appl. Publ. No. 2009/0290167 A1, which is incorporated herein by this reference in its entirety.

A bandpass filter 152 electronically filters the electronic signal from the detector 150 indicative of the time-varying intensity of the swept optical signal. The passband of the filter 152 corresponds to the cavity round trip frequency, if the laser 100 is to be constrained to function with only a single pulse circulating in the laser cavity, or a harmonic of this frequency, if the laser 100 is to be constrained to function with multiple pulses simultaneously circulating in the laser cavity. This frequency corresponds to the time required for light to make a round trip in the cavity of the laser 100. In the illustrated laser, this corresponds to twice the time required for light to propagate from the tunable filter 412, including the optical delay imparted by the filter itself, at one end of the cavity to the output reflector 405 at the end of the pigtail 406 or a reflector installed on the bench B, in the short cavity embodiments. For typical swept laser cavity dimensions, this frequency can be in the several GigaHertz (GHz) range.

In gated mode locking the laser when tuning operates with multiple pulses circulating in the cavity without the regenerative mode locking. The gated mode locking is implemented by selecting the passband of the bandpass filter 152 to electronically filter the feedback from the detector 150 to constrain the laser to operate with the desired number of pulses, which is less than the pulses circulating in the cavity. In one example, the laser is constrained to function with only a single pulse circulating in the laser cavity.

In some embodiments, a delay or specifically a tunable delay 154 is used to delay the electronic signal corresponding to the time-varying intensity of the swept optical signal. This delay 154 is used so that the regenerative feedback has the proper phase to control the pulse or pulses within the laser cavity.

In some embodiments, the delay includes an optical delay. In such embodiments, the photo diode detector 150 receives the swept optical signal via an optical fiber or other optical delay element or a tunable optical delay element or line.

An amplifier 156 is further typically used in the feedback loop for a bias T current modulation system 455. In more detail, a laser bias current source 456 supplies a direct current for the bias current supplied to the SOA 410. This current passes through an inductor 458 of the bias T 455.

The signal amplifier 156 is supplied through a capacitor 462 such that the capacitor 462 in combination with the inductor 458 yield a modulated bias current 490 that is delivered to the SOA 410 via a package impedance-matched stripline 464 and a bench-mounted impedance-matched stripline 466.

One difference between FDMLs and the regenerative swept mode locked lasers described here is how the mode locking is performed. For an FDML, the laser wavelength periodic sweep rate, given by the tunable filter sweep rate, is equal to the laser cavity roundtrip rate or its multiple, say a factor of 2 to 10 multiple. For 100 kHz typical sweep rate this requires kilometer or more long optical laser cavities. In contrast, for these relatively short-cavity OCT swept-mode locked lasers, the laser periodic wavelength sweep rate, e.g. 20-100 kHz, which is also given by the tunable filter sweep rate, is several orders of magnitude smaller than the laser cavity roundtrip rate, which is, for example, in the 1-3 GHz range. Here, wavelength sweep rate is very much smaller, by several orders of magnitude, than the laser cavity roundtrip rate, where for FDML the two rates are equal or a small multiple of each other.

Figure 2:
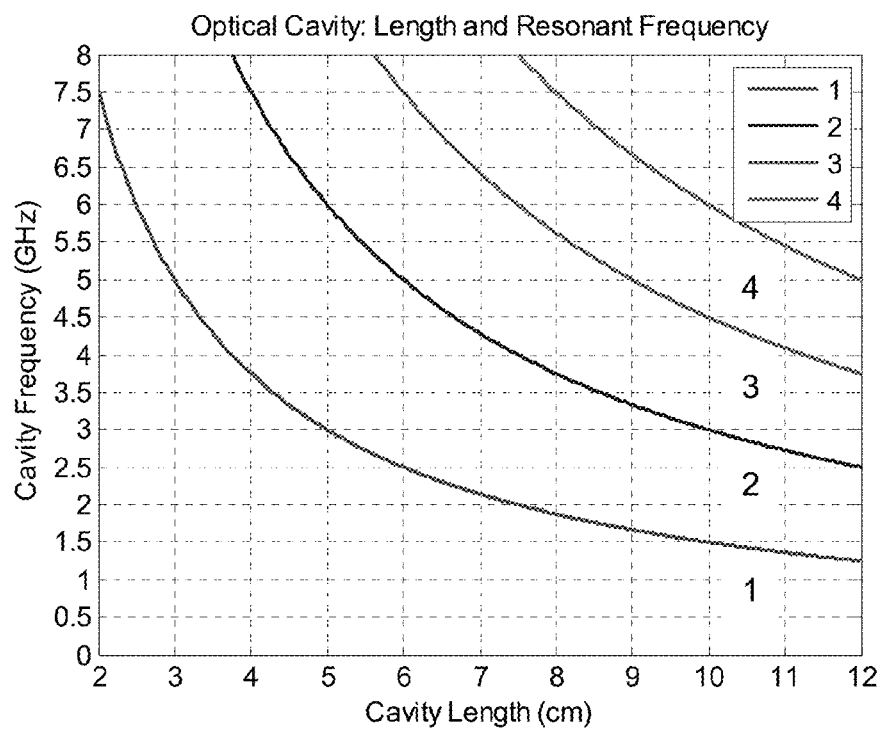
FIG. 2 is a plot of laser cavity resonant frequency in GigaHertz for 1-4 pulses circulating in the laser cavity as a function of the effective cavity length in centimeters (cm) in a vacuum.

FIG. 2 illustrates the relationship between the cavity frequency and thus the time-varying intensity of the swept optical signal. Generally, for cavity lengths of a few centimeters, the frequency of the swept optical signal is at least several Gigahertz, or higher when multiple pulses, such as 2-4 pulses are circulating within the laser cavity.

Figure 3:
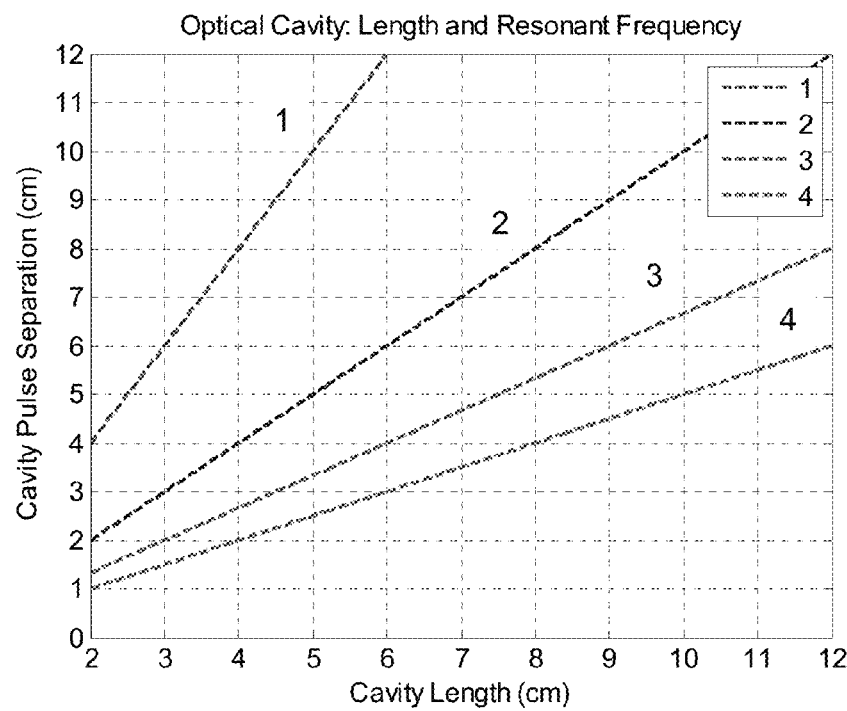
FIG. 3 is a plot of pulse separation in centimeters for 1-4 pulses circulating in the laser cavity as a function of the effective cavity length in centimeters in a vacuum.

FIG. 3 illustrates the physical separation between the pulses for the equivalent vacuum when one or multiple pulses are circulating in the laser cavity.

Figure 4:
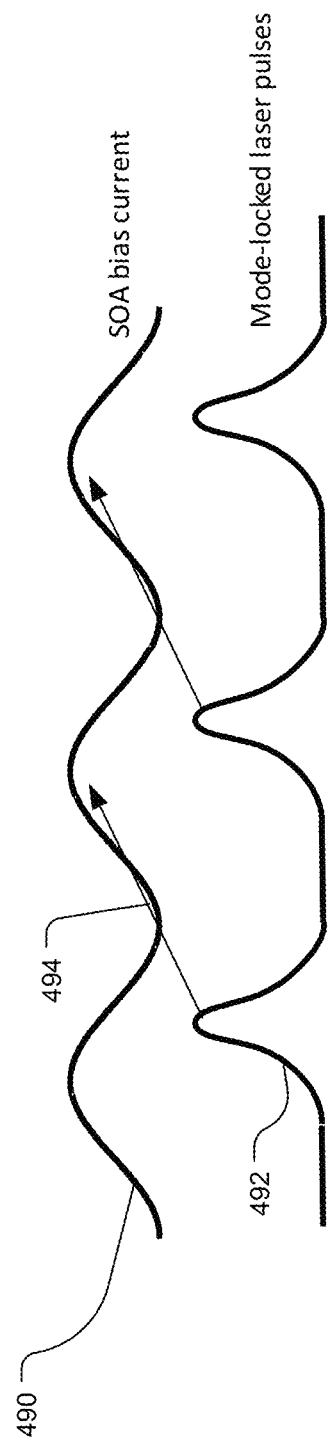
FIG. 4 is a schematic plot of the modulated signal (e.g., SOA bias current) of the regenerative mode locking system and the laser pulses circulating in the laser cavity as a function of time.

FIG. 4 illustrates the operation of the regenerative mode-locked laser swept source 100. A modulated bias current 490 is delivered to the SOA 410 in order to modulate the gain of the laser cavity. In the illustrated example, the bias current is generally sinusoidal. The frequency of the bias current is determined by the time-varying intensity of the swept optical signal as detected by detector 150. The delay 494 between the pulse detection and the bias current peaks corresponds to the electronic and/or optical delay in the feedback path of the regenerative mode locking system, including the delay provided by the tunable delay 154 to ensure that the pumping provided by the SOA gain element 410 is synchronous with the pulses arrival at the SOA 410. In some examples, the delay is greater than 100% of the period of the pulses to address the situation where the minimum electronic delay is much larger than the optical delay or round trip cavity travel time.

To elaborate further, the effective cavity length of swept lasers can change over the sweep because of pulse saturation dynamics in the gain medium, changes in tunable filter group delay, and physical cavity length changes. The more the cavity length changes, and the faster the cavity length changes, the more important it is to keep the feedback loop length short by minimizing electrical and optical delays. Having said that, the loop length also needs to be set so that the feedback to the optical modulation element has a phase (time delay, roughly speaking) that promotes regeneration. Once that optimum is found, increasing or decreasing the time delay by a few optical cavity round trip times should work similarly.

This bias current modulation constrains the laser 100 to operate in a mode locked regime and controls the number of pulses, typically one or more pulses 492, that circulate in the laser's cavity. The regenerative mode locking system generates the modulated bias current signal 490 that constrains the tunable laser 100 to operate in the mode locked condition. Specifically, the cavity's gain is modulated synchronously with the mode-locked laser pulses 492 traveling in the cavity of the laser 100. This prevents chaotic pulsation and cleans up the frequency sweep k-clock jitter and relative intensity noise (RIN).

In other embodiments, the mode locking system is driven with more complex waveforms (non-sinusoids) that are synchronized to the round trip of the cavity.

Figure 5:
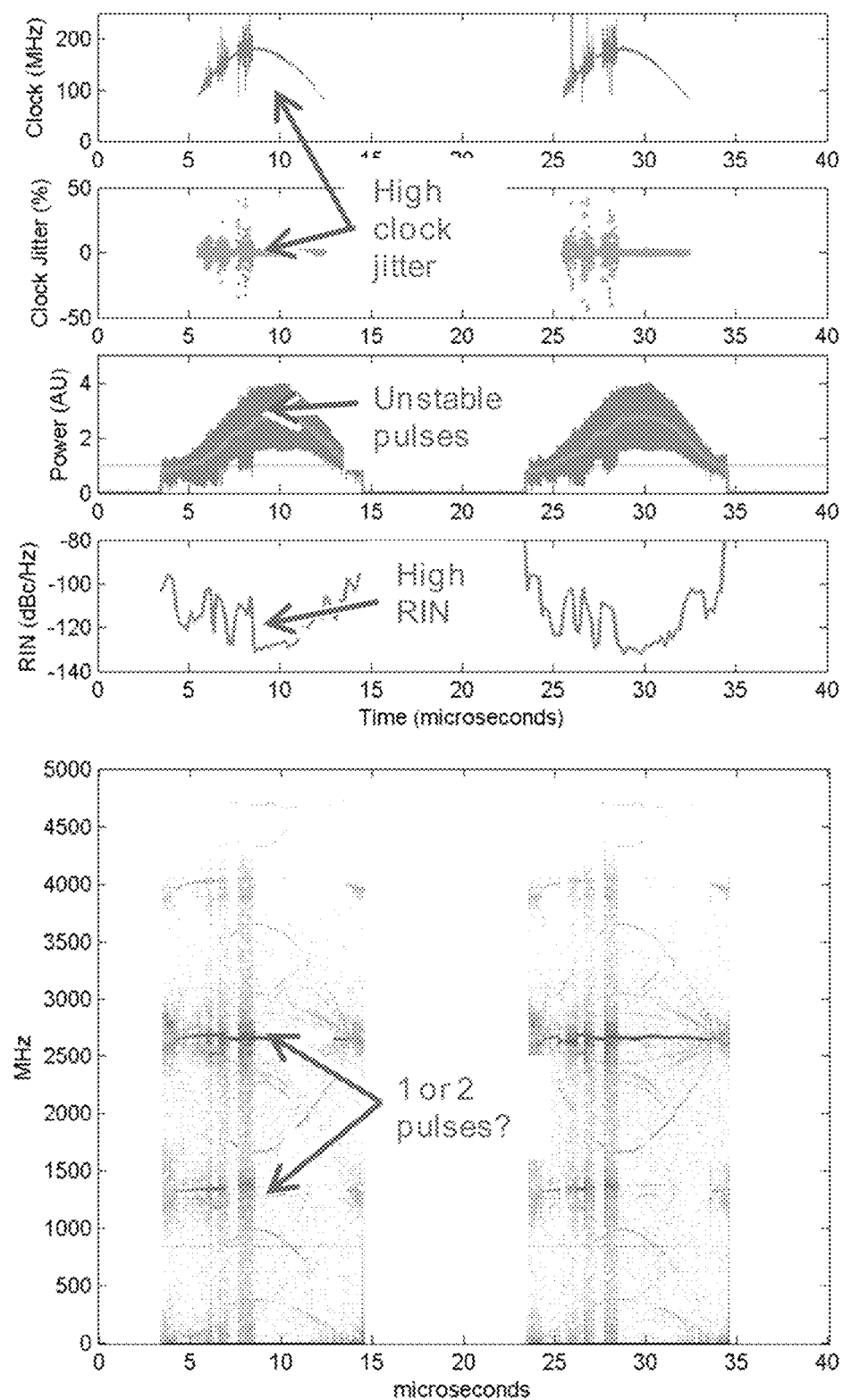
FIG. 5 contains five plots of experimental data on a common timescale in microseconds: clock frequency in MegaHertz, clock jitter in percent, laser power output in arbitrary units, relative intensity noise (RIN) (dBc/Hz), and a spectrogram showing the frequency content vs. time of the laser's instantaneous power output, illustrating a tunable laser source exhibiting swept mode locking during scanning over the tuning band but without any regenerative stabilization.

FIG. 5 contains plots of the k-clock frequency and clock jitter of the swept optical signal for the case where there is no active modulation of the SOA current. The k-clock exhibits high levels of jitter suggesting poor tuning performance. Further, the power output of the swept optical signal from tunable laser is highly unstable over the scan. RIN is also high. The spectrogram shows the existence of pulses in the swept optical signal at approximately 2600 and 1300 MHz. The energy distribution seems to vary over the course of the scan through the tuning band of the laser.

This uncontrolled pulse behavior during the course of the scan of the swept optical signal through the tuning band is believed to be instigated by the changing characteristics of the laser cavity over the tuning band. A strong factor is the changing effective delay of reflection from the Fabry Perot filter 412. In one example, the group delay length of filter reflection changes from approximately 11 millimeters (mm) in the center of the tuning band to approximately 5 mm at the edges of the 100 nm or wider tuning band. This is due to a drop in the filter's finesse by a factor of two from the center to the edges of the band.

In uncontrolled lasers, the number of pulses in the laser cavity due to swept mode locking has been observed to change between forward and backward sweeps, and can even switch in the middle of a sweep as illustrated.

Figure 6B:
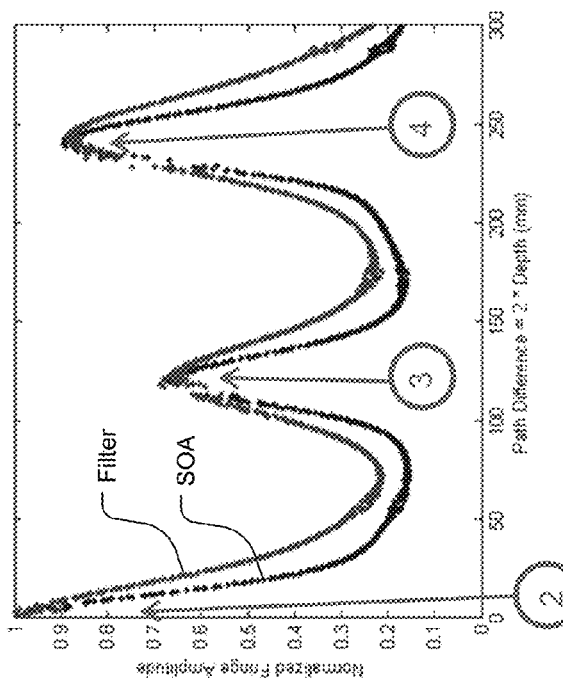
FIG. 6B is a plot of normalized fringe amplitude from a test interferometer as a function of depth in millimeters, illustrating a tunable laser source exhibiting swept mode locking during scanning over the tuning band but without any regenerative stabilization.
Figure 6A:
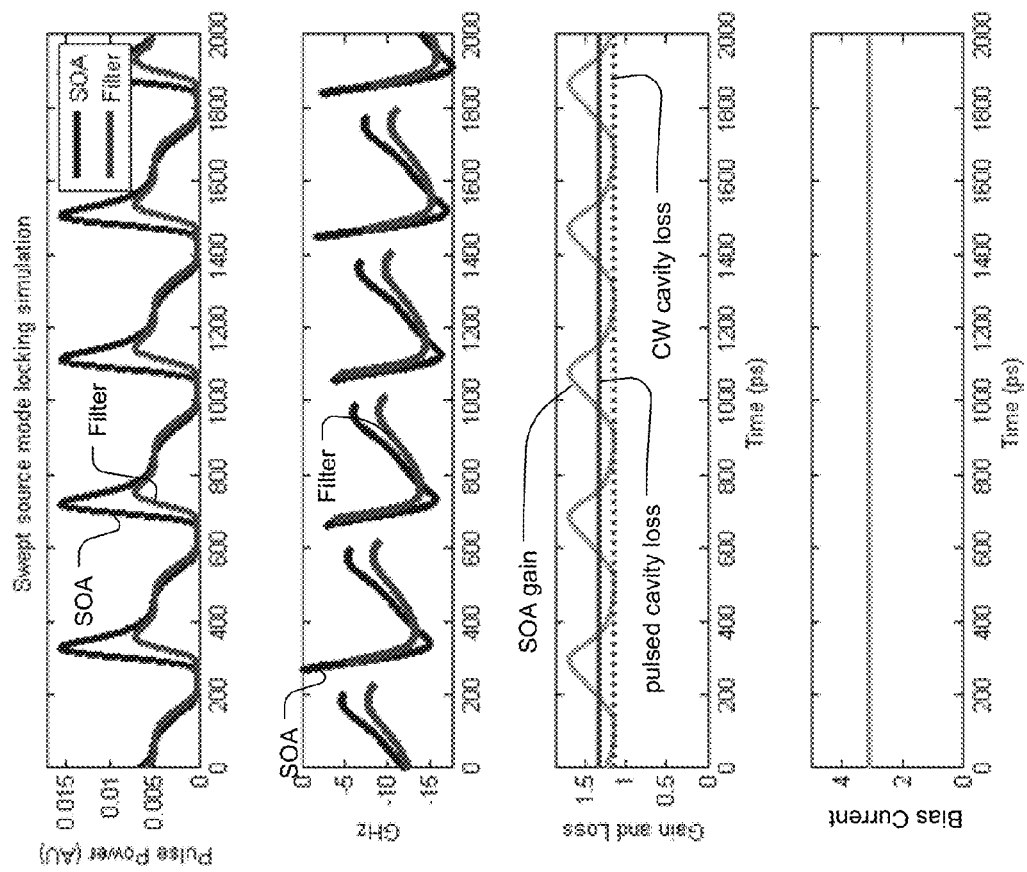
FIG. 6A contains four plots from a computer simulation on a common timescale in picoseconds: optical power for light exiting the SOA 410 and the Fabry-Perot tunable filter 412, the instantaneous optical frequency change of the pulses in GigaHertz (GHz), the gain from the SOA 410 and cavity loss, and the bias current to the SOA 410.

FIGS. 6A and 6B are the results of a computer simulation. It shows a tunable laser exhibiting swept mode locking without gain modulation. In this case, the laser operates with 2 pulses per cavity round trip.

The correlation plots of FIG. 6B, one for light exiting the SOA 410 and one for light exiting the tunable filter 412, are computer simulations of a swept source coherence length measurement, but carried out to extreme path differences. The usual coherence length measurement occurs at path differences near zero (2). At 120 mm (3) the pulses are interfering with their neighbors. At 240 mm (4) the pulses are interfering with pulses 1 cavity round trip away, which is two pulses apart.

These secondary coherences (3) (4) can sometimes be a problem in practical OCT systems where small stray reflections at lengths nearly corresponding to the cavity length or fractions thereof (depending on the number of pulses per round trip) can produce artifacts in the OCT image. It is helpful to eliminate these as much as possible. In the current embodiments, these pulses are eliminated by control selection of the passband of the filter 152. That is by blocking regenerative feedback at undesired harmonics, the number of pulses is reduced or constrained to operate with only a single pulse in the laser cavity.

Figure 7:
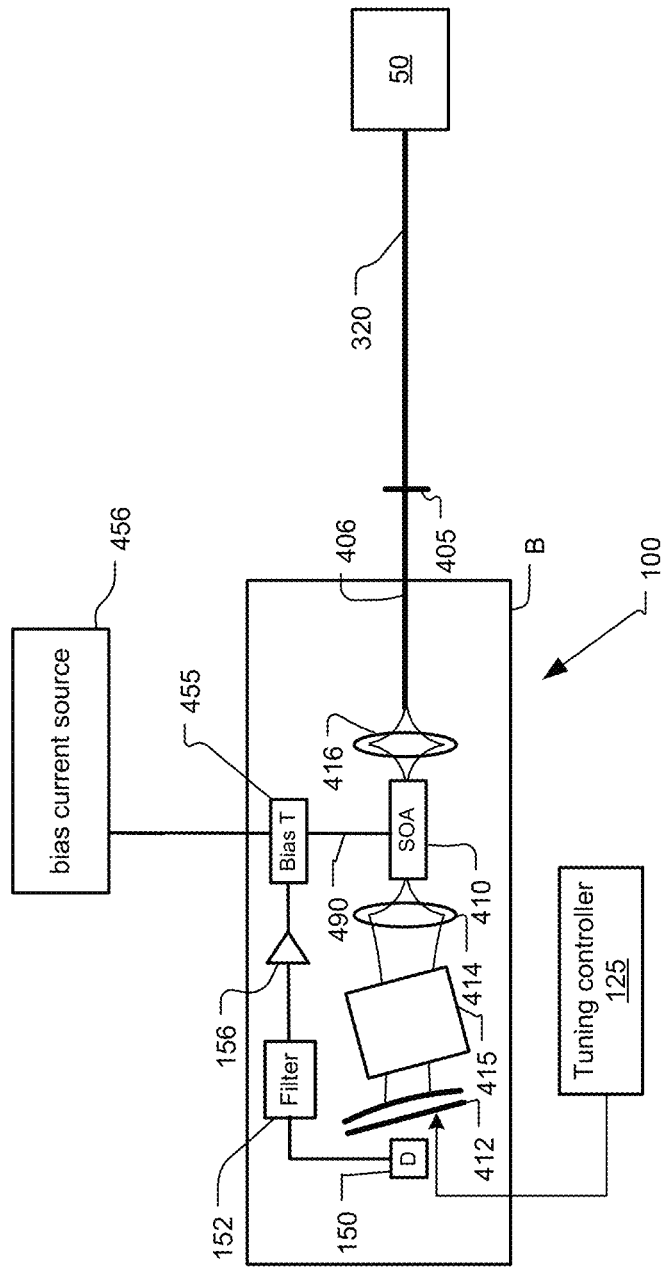
FIG. 7 is a schematic diagram of a regenerative mode-locked laser swept source for optical coherence analysis according to a second embodiment in which the mode locking system is integrated on the optical bench with the laser swept source.

FIG. 7 illustrates a second embodiment in which the regenerative mode locking system is implemented on the optical bench B with the components of the laser 100. In this example, the electronic delay in regenerative feedback path is kept small. This reduces or even eliminates the need for the electronic delay 154 in some examples.

Figure 8:
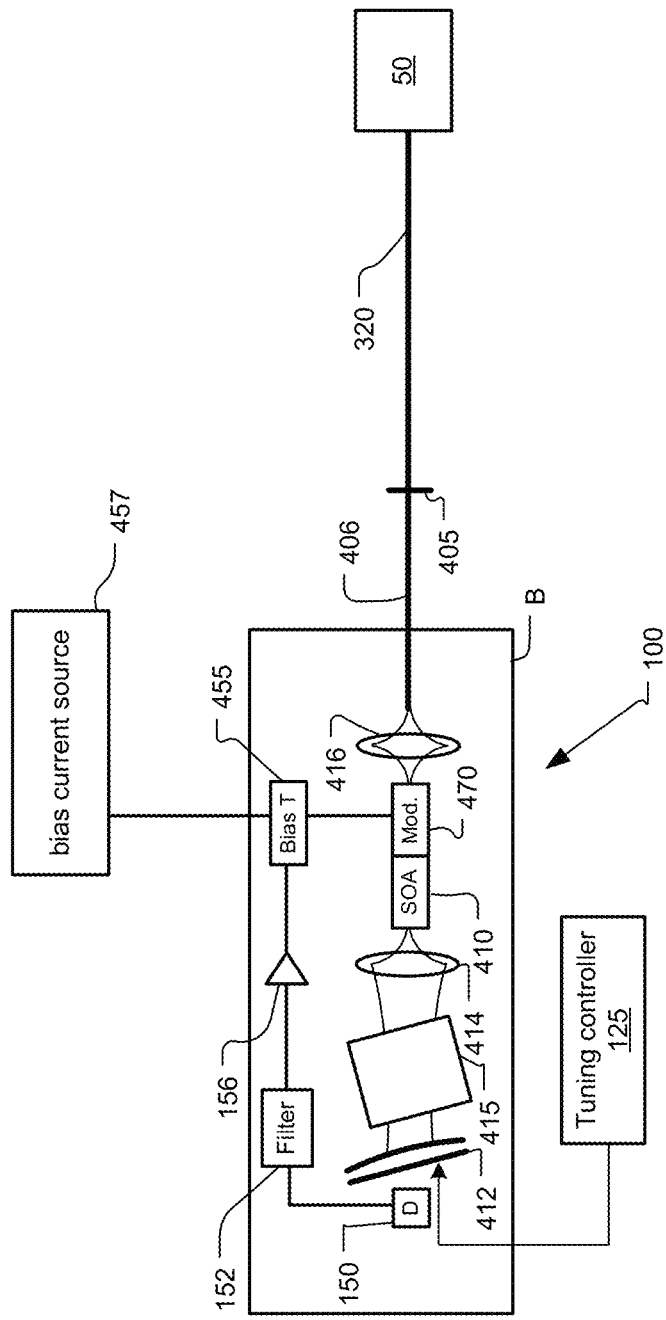
FIG. 8 is a schematic diagram of a regenerative mode-locked laser swept source for optical coherence analysis according to a third embodiment in which the mode locking system includes an intracavity phase and/or gain modulation system.

FIG. 8 illustrates a third embodiment in which the regenerative feedback system modulates a phase and/or gain/loss of the optical signals circulating in the laser cavity. In more detail, a phase modulator 470 is added into the cavity, preferably towards one end of the cavity to control the mode locked operation of the laser. In one embodiment, the phase modulator 470 is installed on the bench B between the SOA 410 and the lens structure 416. In the preferred embodiment, it is a semiconductor chip that is integral with the SOA chip 410 and specifically a phase modulation section to which a separate, modulated bias current or Voltage is supplied to thereby yield a two-section SOA (gain, phase). Integrated phase modulators generally work forward biased through current injection, but reverse biased types also exist.

In other examples, the phase modulator 470 is an external modulator, such as $LiNbO_3$.

Preferably, the modulation to the phase modulator 470 is generated as described previously, by detecting via detector 150 the intensity of the optical swept signal and then filtering via bandpass filter 152 and amplifying via amplifier 156. The signal is supplied to the bias T 455 that generates a modulated signal at a harmonic of the cavity round trip frequency. A bias current source 457 produces the bias current or voltage 490 that is delivered to the phase modulator 470.

Typically in this example, the bias current source for the SOA 410 supplies a DC, unmodulated, signal.

The phase modulator 470 imparts a frequency shift of its own, $(1/2\pi)d\Phi/dt$, as the pulse passes through it. This frequency shift can be positive or negative depending on the pulse's timing. Since the shift can be positive, counteracting the negative frequency shift from gain medium saturation, stable operation can be achieved for positive tuning rates.

The phase modulator 470 is driven at a high harmonic of the round trip time of the long cavity in one example. Complex waveforms and harmonics of the cavity round trip frequency can be also used to drive the phase modulator. In the case of sinusoidal modulation, the modulated phase is $\Phi_{peak} \cos(2\pi f_{mod} t)$. The phase modulator imparts a maximum frequency shift per round trip of $\Phi_{peak} \cdot f_{mod}$. The sign and magnitude of the frequency shift depends on the timing of the pulse with respect to the phase modulation waveform.

In general, the phase modulator 471 can be driven with more complex waveforms (non-sinusoids) that are synchronized to the round trip of the cavity. This permits both blue and red shifting of pulses to thereby either change the tuning direction or reduce the tuning rate by red shifting some pulses and blue shifting others to reduce the overall tuning rate.

Figure 9:
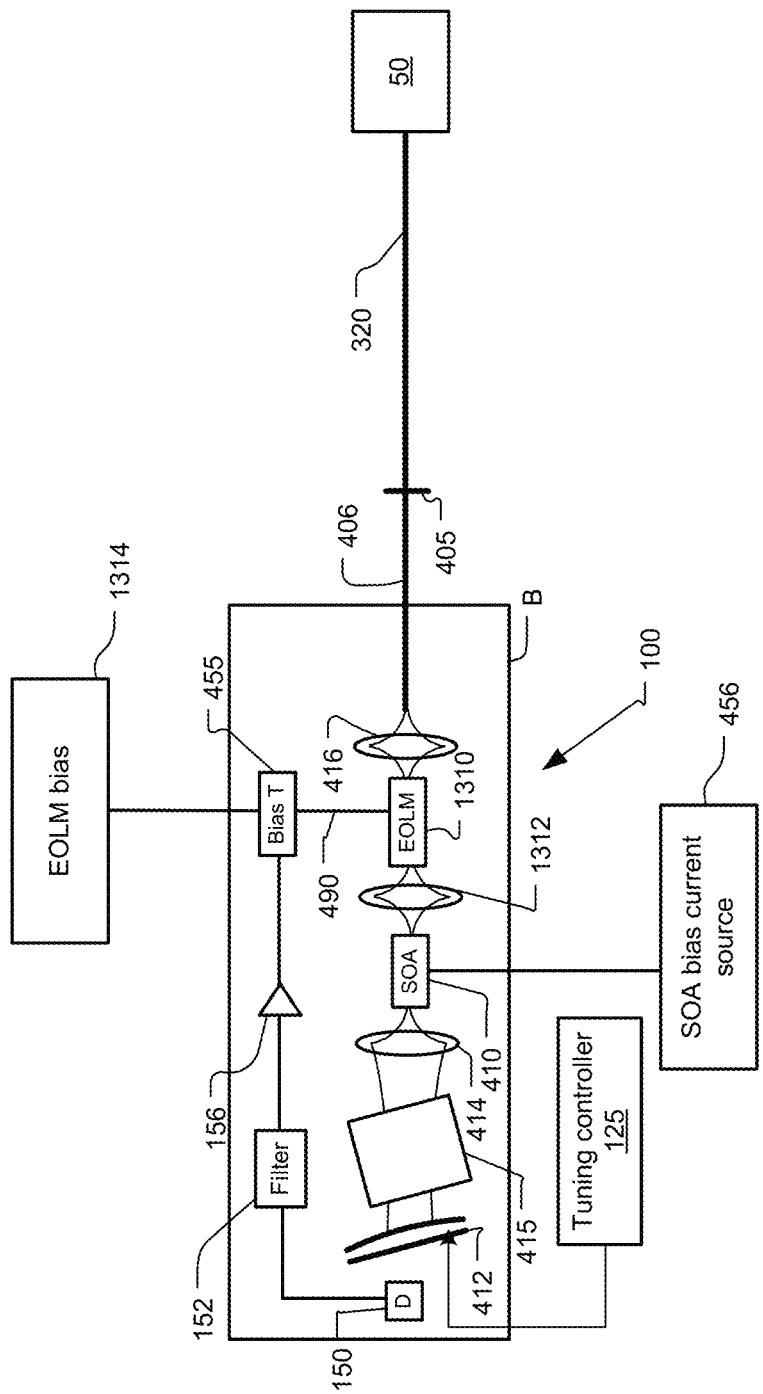
FIG. 9 is a schematic diagram of a regenerative mode-locked laser swept source for optical coherence analysis according to a fourth embodiment in which the mode locking system includes an intracavity cavity loss modulation system.

FIG. 9 illustrates another embodiment in which the regenerative mode locking system is implemented as an in-cavity electro-optic loss modulator 1310 in a linear cavity laser swept source configuration.

In more detail, an electro-optic loss modulator 1310 is added into the cavity, preferably towards one end of the cavity, to control the mode locked operation. It is used to modulate the net gain of the laser cavity. In one embodiment, the electro-optic loss modulator (EOLM) 1310 is installed on the bench B between the SOA 410 and the lens structure 416. An intervening lens 1312 couples light between the SOA 410 and the EOLM 1300.

Preferably, the modulation to the electro-optic loss modulator 1310 is supplied as described previously using a bias T 455 with a bias source 1314 to produce a modulated bias current or voltage 490 that is delivered to the electro-optic loss modulator 1310.

Typically in this example, the bias current source 456 for the SOA 410 supplies a DC, unmodulated, signal.

In the illustrated embodiment, the loss modulation is performed by a high-speed EOLM modulator 1310. In other embodiments, waveguide Mach-Zehnder loss modulators, standing wave acousto-optic "mode-lockers", electro-absorption modulators, in either linear or ring configurations are implemented. Most technologies mandate that the modulation be separate from the SOA 410, although some technologies allow integration with the SOA chip.

Figure 10A:
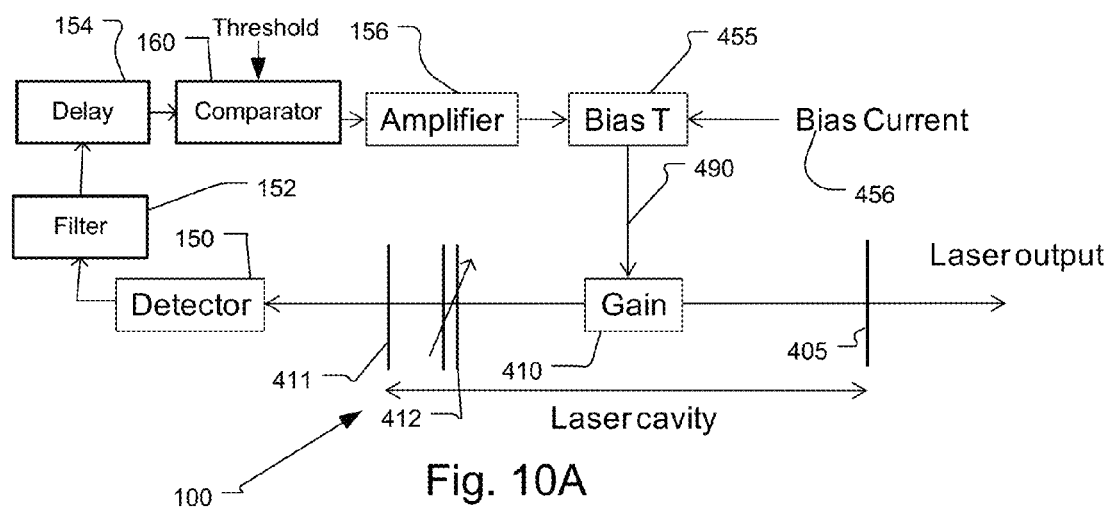
FIGS. 10A and 10B are schematic diagrams of a regenerative mode-locked laser swept source for optical coherence analysis including a comparator in the feedback from the detector to control mode-locked operation of laser swept source in response to the time-varying intensity of swept optical signal for linear and ring cavity lasers, respectively.

FIG. 10A illustrates another feedback loop for mode locking. In this example, the laser 100 is shown schematically. The laser cavity including the gain medium 410 and the tuning element 412, along with two reflectors 411, 405 that defined the ends of the laser cavity. In this example, the tunable element 412 is shown in a transmissive configuration requiring a separate reflector 411. The detector 150 detects the portion of the swept optical signal that is transmitted through reflector 411. As described previously, the electrical response of the detector 150 is filtered by a bandpass filter 152. A delay 154, if required, delays the electronic signal to ensure synchronous pumping. Next, a comparator 160 compares the electronic signal corresponding time varying intensity of the swept optical signal to a threshold. This converts the regenerative feedback to a square wave that is then amplified in the amplifier 156 and applied to bias T 455. This results in a square wave modulation to the gain medium 410.

These non linear elements enable the driving of the system with more complex waveforms. These complex waveforms are "triggered" or "synchronized" to the mode beat from the filtered photodiode signal. More specifically, a square wave with a variable duty cycle is a good example. This could be done by triggering a one-shot of programmable time duration from the cavity beat waveform.

Figure 10B:
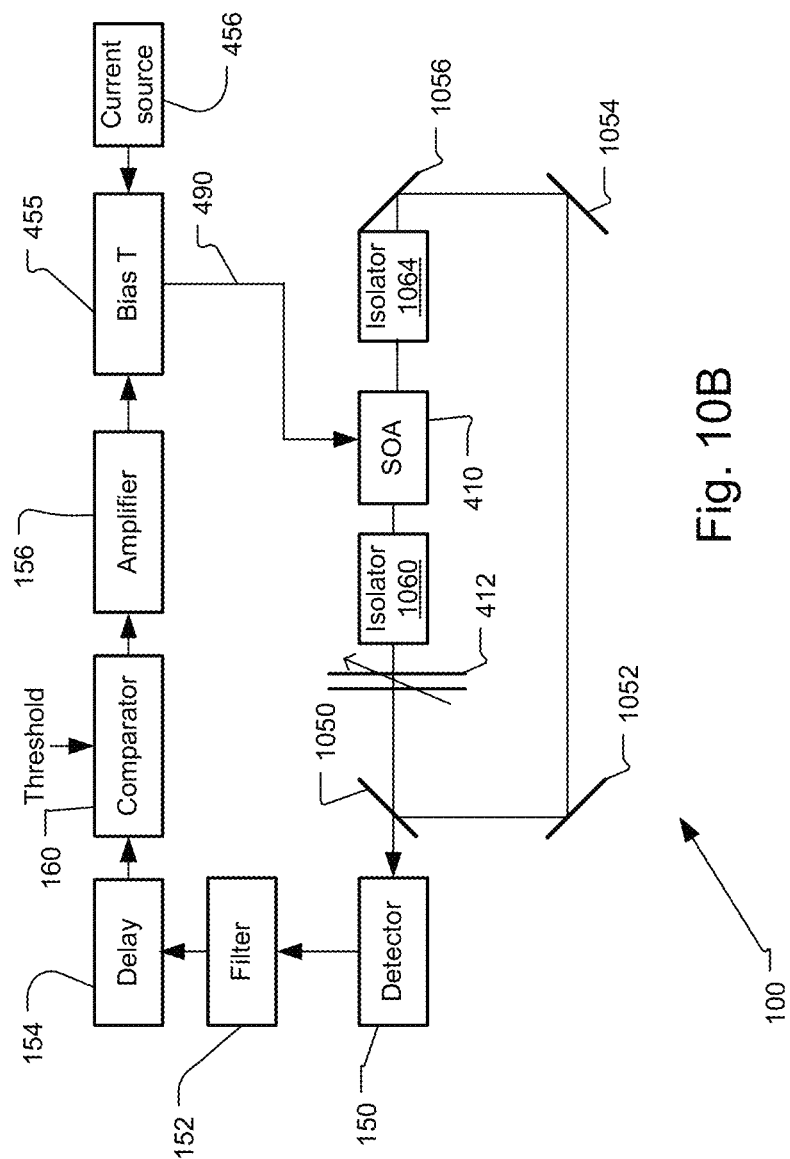

FIG. 10B shows a related embodiment in which the laser 100 has a ring cavity configuration comprising a series of four reflectors 1050, 1052, 1054, 1056. A portion of the light circulating in the cavity is transmitted through mirror 1050 to be detected by the detector 150. Typically, isolators 1060, 1064 are further included in the cavity to ensure that light propagates in the desired counterclockwise direction.

Figure 11B:
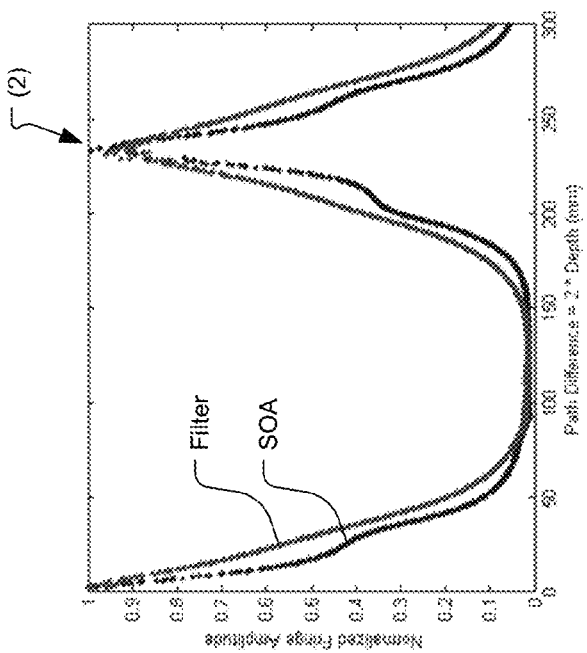
FIG. 11B is a plot of normalized fringe amplitude from a test interferometer as a function of depth in millimeters, illustrating the performance of a tunable laser with regenerative mode locking during scanning over the tuning band in which only one pulse is allowed to circulate within the laser cavity by application of a square wave SOA bias current to thereby implement gated regenerative swept mode locking.
Figure 11A:
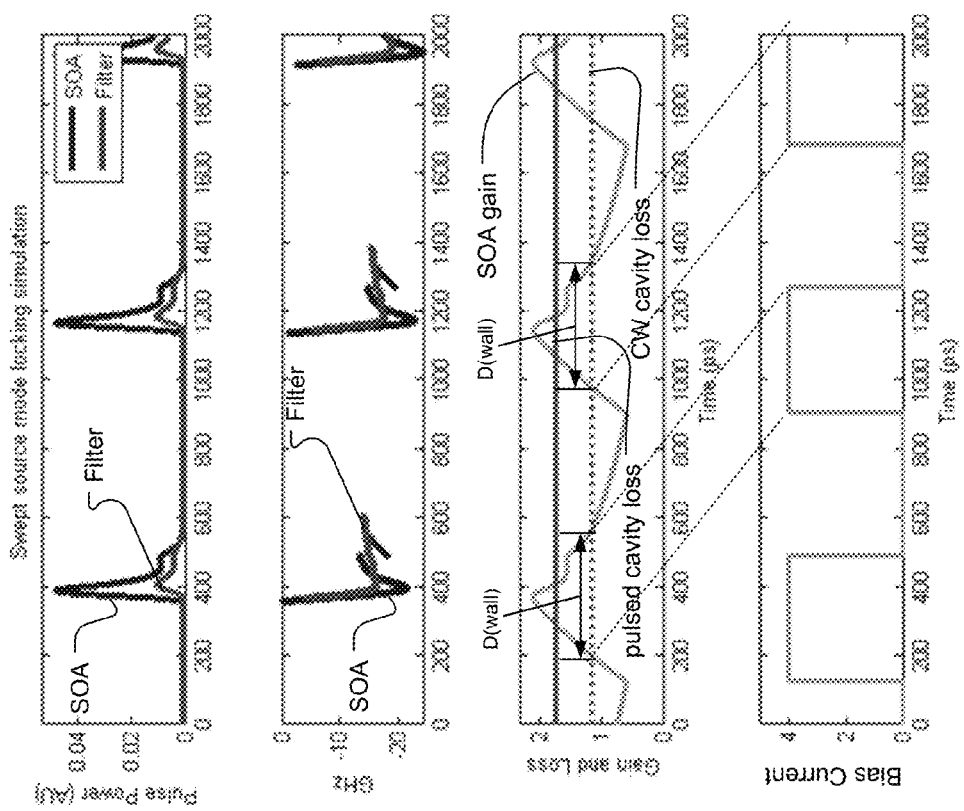
FIG. 11A contains four plots from a computer simulation on a common timescale in picoseconds: optical power for light exiting the SOA 410 and the Fabry-Perot tunable filter 412, the instantaneous optical frequency change in GigaHertz (GHz), the gain from the SOA 410, and the bias current to the SOA 410.

FIGS. 11A and 11B are the results of another computer simulation. It shows a tunable laser with stabilized swept mode locking using square wave driving signal.

The swept optical signal from the laser 100 has repeated coherence peaks at the pulse spacing. The square pump pulse bias current 490 is applied to the SOA 410, which is synchronized with the round-trip time of the cavity.

Figure 12:
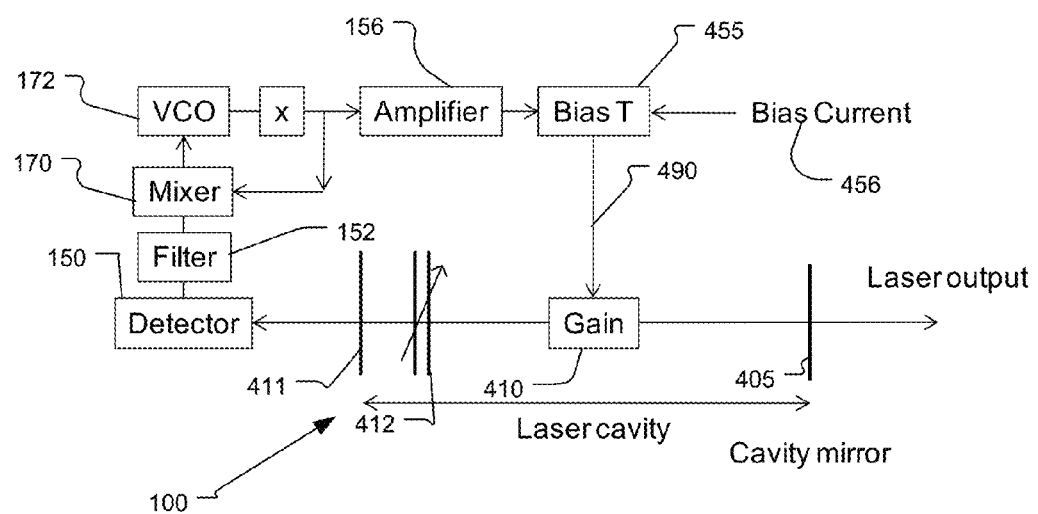
FIG. 12 is a schematic diagram of a regenerative mode-locked laser swept source for optical coherence analysis including a phase locked loop in the feedback from the detector to control mode-locked operation of laser swept source in response to the time-varying intensity of swept optical.

FIG. 12 shows another embodiment of the regenerative feedback loop. In this example, a phase locked loop circuit is used. Specifically, the output from the bandpass filter 152 is provided to a mixer 170. Mixer provides the input to a voltage controlled oscillator 172. This output is then fed back to the mixer 170. This produces a phase locked loop that oscillates synchronously with the time varying intensity of the swept optical signal generated in the laser cavity of the laser 100.

The output from the phase lock loop is provided to the amplifier 156 and then through a bias T 455 to drive the gain element 410.

Figure 13B:
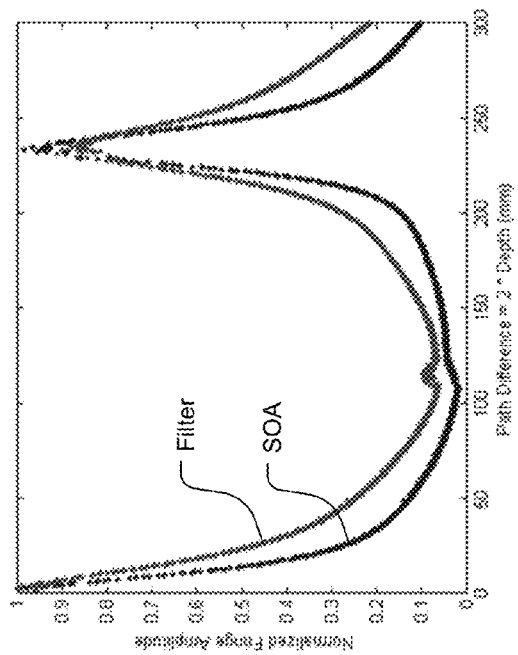
FIG. 13B is a plot of normalized fringe amplitude from a test interferometer as a function of depth in millimeters, illustrating the performance of a tunable with stabilized mode locking during scanning over the tuning band in which only pulse is allowed to circulate within the laser cavity by application of a sinusoidal SOA bias current.
Figure 13A:
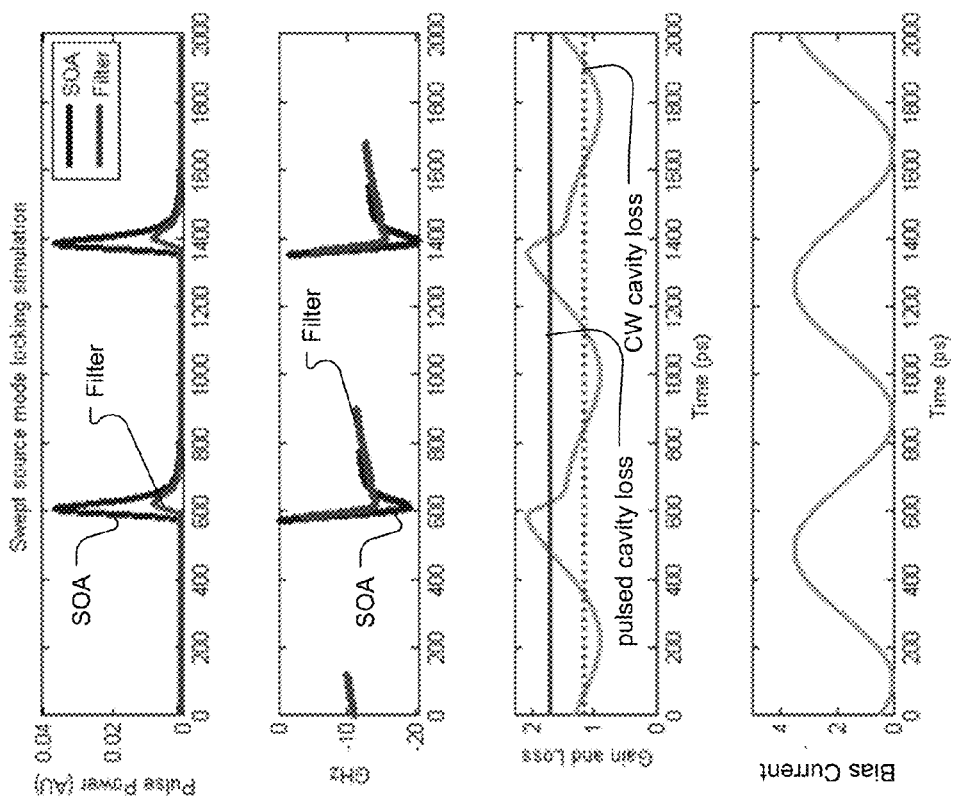
FIG. 13A contains four plots from a computer simulation on a common timescale in picoseconds: optical power for light exiting the SOA 410 and the Fabry-Perot tunable filter 412, the instantaneous optical frequency change in GigaHertz (GHz), the gain from the SOA 410, and the bias current to the SOA 410.

FIGS. 13A and 13B are the results from another computer simulation. It shows a tunable laser with regenerative swept mode locking.

A sinusoidal bias current 490 shaped by the phase locked loop is applied to the SOA 410, which is synchronized with the round-trip time of the cavity. This constrains the laser 100 to operate with one pulse per round trip. In this case, there is a secondary coherence peak only at 240 mm.

Figure 14:
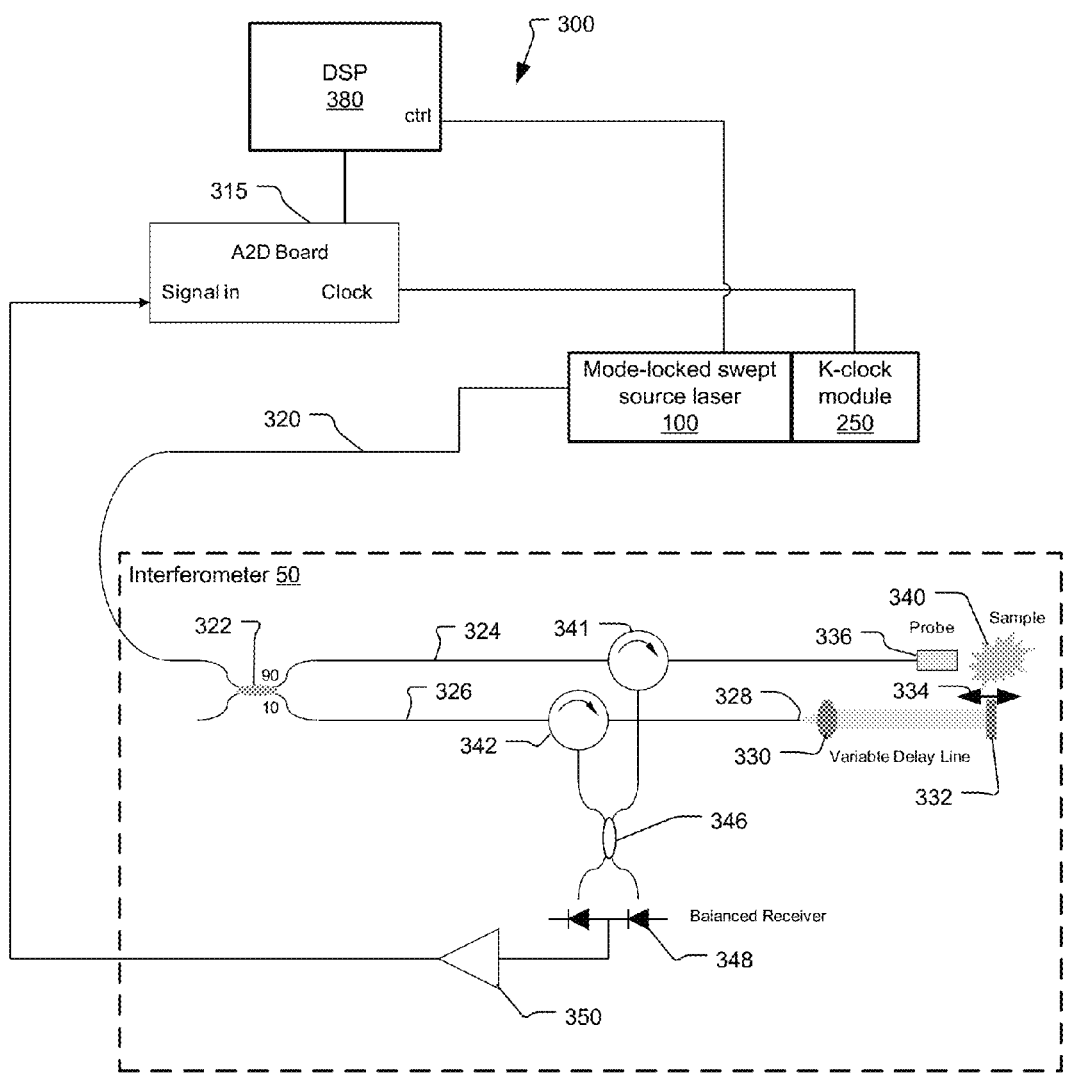
FIG. 14 is a schematic view of an OCT system incorporating the regenerative mode-locked laser swept source according to an embodiment of the invention.

FIG. 14 shows an optical coherence analysis system 300 using the mode locked laser source 100, which has been constructed according to the principles of the present invention.

The tunable laser swept source 100 with stabilized mode locked operation generates the tunable or swept optical signal on optical fiber 320 that is transmitted to interferometer 50. The swept optical signal scans over a scanband with a narrowband emission.

Preferably, a k-clock module 250 is used to generate a clocking signal at equally spaced optical frequency increments as the optical signal is tuned or swept over the scan or tuning band.

In the current embodiment, a Mach-Zehnder-type interferometer 50 is used to analyze the optical signals from the sample 340. The tunable signal from the swept laser source 100 is transmitted on fiber 320 to a 90/10 optical coupler 322. The combined tunable signal is divided by the coupler 322 between a reference arm 326 and a sample arm 324 of the system.

The optical fiber of the reference arm 326 terminates at the fiber endface 328. The light exiting from the reference arm fiber endface 328 is collimated by a lens 330 and then reflected by a mirror 332 to return back, in some exemplary implementations.

The external mirror 332 has an adjustable fiber to mirror distance (see arrow 334), in one example. This distance determines the depth range being imaged, i.e. the position in the sample 340 of the zero path length difference between the reference arm 326 and the sample arm 324. The distance is adjusted for different sampling probes and/or imaged samples. Light returning from the reference mirror 332 is returned to a reference arm circulator 342 and directed to a 50/50 fiber coupler 346.

The fiber on the sample arm 324 terminates at the sample arm probe 336. The exiting swept optical signal is focused by the probe 336 onto the sample 340. Light returning from the sample 340 is returned to a sample arm circulator 341 and directed to the 50/50 fiber coupler 346. The reference arm signal and the sample arm signal are combined in the fiber coupler 346 to generate an interference signal. The interference signal is detected by a balanced receiver, comprising two detectors 348, at each of the outputs of the fiber coupler 346. The electronic interference signal from the balanced receiver 348 is amplified by amplifier 350.

An analog to digital converter system 315 is used to sample the interference signal output from the amplifier 350. Frequency clock and sweep trigger signals derived from the k-clock module 250 of the mode-locked swept source 100 are used by the analog to digital converter system 315 to synchronize system data acquisition with the frequency tuning of the swept source system 100.

Once a complete data set has been collected from the sample 340 by spatially raster scanning the focused probe beam point over the sample, in a Cartesian geometry, x-y, fashion or a cylindrical geometry theta-z fashion, and the spectral response at each one of these points is generated from the frequency tuning of the mode-locked swept source 100, the digital signal processor 380 performs a Fourier transform on the data in order to reconstruct the image and perform a 2D or 3D tomographic reconstruction of the sample 340. This information generated by the digital signal processor 380 can then be displayed on a video monitor.

In one application, the probe is inserted into blood vessels and used to scan the inner wall of arteries and veins. In other examples, other analysis modalities are included in the probe such as intravascular ultrasound (IVUS), forward looking IVUS (FLIVUS), high-intensity focused ultrasound (HIFU), pressure sensing wires and image guided therapeutic devices.

While this invention has been particularly shown and described with references to preferred embodiments thereof, it will be understood by those skilled in the art that various changes in form and details may be made therein without departing from the scope of the invention encompassed by the appended claims. For example, although the invention has been described in connection with an OCT or spectroscopic analysis only, the invention could also be applied along with IVUS, FLIVUS, HIFU, pressure sensing wires and image guided therapeutic devices.

What is claimed is:

1. An optical coherence imaging method, comprising:
providing a laser swept source to generate a swept optical signal in a laser cavity that is less than a meter long;
detecting time-varying intensity of the swept optical signal;
using the detected time-varying intensity of the swept optical signal as feedback to control a mode-locked operation of the laser swept source by modulating an intracavity element in the laser cavity based on the roundtrip travel time of light in the laser cavity;
transmitting the swept optical signal to an interferometer having a reference arm and a sample arm, in which a sample is located;
combining the swept optical signal returning from the sample arm and the reference arm to generate an interference signal;
detecting the interference signal; and
generating image information of the sample from the detected interference signal.

2. A method as claimed in claim 1, wherein controlling the mode-locked operation of the laser swept source comprises controlling a bias current to an optical gain element that amplifies light in the laser cavity of the laser swept source in response to the time-varying intensity of the swept optical signal.

3. A method as claimed in claim 1, wherein controlling the mode-locked operation of the laser swept source comprises modulating a phase of optical signals in the laser cavity of the laser swept source in response to the time-varying intensity of the swept optical signal.

4. A method as claimed in claim 1, wherein controlling the mode-locked operation of the laser swept source comprises controlling the laser cavity of the laser swept source to reduce a number of pulses circulating in the laser cavity.

5. An optical coherence imaging method, comprising:
providing a laser swept source to generate a swept optical signal in a laser cavity that is less than a meter long;
detecting time-varying intensity of the swept optical signal;
using the time-varying intensity of the swept optical signal as feedback to control a mode-locked operation of the laser swept source;
transmitting the swept optical signal to an interferometer having a reference arm and a sample arm, in which a sample is located;
combining the swept optical signal returning from the sample arm and the reference arm to generate an interference signal;
detecting the interference signal; and
generating image information of the sample from the detected interference signal; and
wherein controlling the mode-locked operation of the laser swept source comprises modulating net gain of the laser cavity of the laser swept source in response to the time-varying intensity of the swept optical signal.

6. An optical coherence analysis system comprising:
a swept laser source for generating a swept optical signal that is frequency tuned over a tuning band in a laser cavity that is less than a meter long, the laser comprising an intracavity element in the laser cavity;
a detector for detecting time-varying intensity of the swept optical signal, in which a mode-locked operation of the swept laser source is controlled by modulating the intracavity element in response to the detected time-varying intensity of the swept optical signal which is based on a roundtrip travel time of light in the cavity;
an interferometer for dividing the swept optical signal between a reference arm and a sample arm leading to a sample; and
a detector system for detecting an interference signal generated from the swept optical signal from the reference arm and from the sample arm.

7. A system as claimed in claim 6, wherein the swept laser source comprises:
a gain medium for amplifying light within the laser cavity of the swept laser source to generate the swept optical signal; and
a tuning element for controlling a frequency of the swept optical signal to sweep across a scanband, and
wherein a gain of the gain medium is modulated in response to the detected time-varying intensity of the swept optical signal.

8. A system as claimed in claim 7, wherein the mode-locked operation of the swept laser source is controlled by modulating bias current to the gain medium in response to the detected time-varying intensity of the swept optical signal.

9. A system as claimed in claim 6, wherein the swept laser source comprises:
a gain medium for amplifying light within the laser cavity of the swept laser source to generate the swept optical signal;
a tuning element for controlling a frequency of the swept optical signal to sweep across a scanband, and
a phase modulator, which is the intracavity element, for controlling a phase of the light within the laser cavity that is modulated in response to the detected time-varying intensity of the swept optical signal.

10. A system as claimed in claim 6, wherein the swept laser source comprises:
a gain medium for amplifying light within the laser cavity of the swept laser source to generate the swept optical signal;
a tuning element for controlling a frequency of the swept optical signal to sweep across a scanband, and
wherein the intracavity element is a cavity gain control element that modulates a net gain of the laser cavity and that is modulated in response to the detected time-varying intensity of the swept optical signal.

11. A system as claimed in claim 6, wherein the intracavity element of the swept laser source is controlled to reduce a number of pulses circulating in the laser cavity.

12. A system as claimed in claim 6, further comprising an amplifier for amplifying the detected intensity of the swept optical signal, and a filter for bandpass filtering the detected intensity of the swept optical signal.

13. A system as claimed in claim 12, wherein a passband center frequency of the filter is inverse of a roundtrip travel time of light in the laser cavity or a multiple thereof.

14. A system as claimed in claim 6, further comprising a delay for delaying the detected intensity of the swept optical signal that is used to control the intracavity element of the swept laser source to delay match the detected intensity of the swept optical signal with pulses circulating within the laser cavity of the swept laser source.

15. A system as claimed in claim 6, further comprising a phase locked loop for controlling the intracavity element and the mode-locked operation of the swept laser source in response to the detected time-varying intensity of the swept optical signal.

* * * * *